United States Patent [19]
Kiyuna et al.

[11] Patent Number: 5,785,653
[45] Date of Patent: *Jul. 28, 1998

[54] SYSTEM AND METHOD FOR PREDICTING INTERNAL CONDITION OF LIVE BODY

[75] Inventors: Tomoharu Kiyuna; Tetsuji Tanigawa; Toshimasa Yamazaki, all of Tokyo, Japan

[73] Assignee: NEC Corporation, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 506,202

[22] Filed: Jul. 24, 1995

[30] Foreign Application Priority Data

Jul. 22, 1994 [JP] Japan .................................. 6-170979
Nov. 8, 1994 [JP] Japan .................................. 6-273818

[51] Int. Cl.$^6$ .......................................... A61B 5/00
[52] U.S. Cl. ................ 600/408; 600/544; 395/21; 395/23; 395/924
[58] Field of Search ............. 128/653.1, 731, 128/920, 923, 924; 395/21, 23, 924; 364/413.02; 600/408, 544

[56] References Cited

U.S. PATENT DOCUMENTS

| | | | |
|---|---|---|---|
| 5,417,211 | 5/1995 | Abraham-Fuchs et al. | 128/653.1 |
| 5,509,424 | 4/1996 | Al-Ali | 128/692 |
| 5,524,086 | 6/1996 | Kiyuna et al. | 128/653.1 |

FOREIGN PATENT DOCUMENTS 2232783 9/1990 Japan .

OTHER PUBLICATIONS

C. D. Yingling et al, "A Subcortical Correlate of P300 in Man", *Electroencephalography and Clinical Neurophysiology*, 1984, pp. 72–76.

James P. Ary ete al, "Location of Sources of Evoked Scalp Potential Corrections for Skull and Scalp Thicknesses", *IEEE Transaction on Biomedical Engineering*, vol. BME-28, No. Jun. 1981, pp. 447–452.

David E. Rumelhart et al, "Learning Internal Representation by Erropr Propagation", *Parallel Distributed Processing*, 1986, pp. 318–362.

*Primary Examiner*—Ruth S. Smith
*Attorney, Agent, or Firm*—Sughrue, Mion, Zinn, Macpeak & Seas, PLLC

[57] ABSTRACT

A live body internal condition predicting and expressing system is capable of predicting the internal condition of a live body on the basis of an electromagnetic field distribution at significantly reduced period. The system comprises an electromagnetic field distribution measuring portion, a training data generating portion generating a plurality of training data on the basis of an electromagnetic field distribution derived from a head model data designating a head model and a predetermined dipole parameter and an internal condition category data describing a relationship between the active region of a brain and the internal condition of the live body, an inference portion deriving a numeric value representative of the active region of the brain from the electromagnetic field distribution in the training data with employing a neural network having predetermined coupling coefficients representative of coupling condition between each unit forming each layer and transforming portion transforming the numeric value representative of the active region in the brain output from said inferencing means into an expression indicative of the internal condition of the live body.

19 Claims, 13 Drawing Sheets

FIG.12

| CATEGORY | BEGINNING POINT OF REGION | END POINT OF REGION | NUMERICAL EXPRESSION OF ACTIVE REGION | INTERNAL CONDITION |
|---|---|---|---|---|
| 1 | $(0,0,0)$ | $(\frac{Rb}{2}, \pi, 2\pi)$ | 1.0 | SURPRISE |
| 2 | $(\frac{Rb}{2}, 0, 0)$ | $(Rb, \pi, 2\pi)$ | $-1.0$ | CALM |

FIG.13

| VALUE OF ELECTROMAGNETIC FIELD | NUMERICAL EXPRESSION OF ACTIVE REGION |
|---|---|
| $(V_1^{(k)}, \cdots, V_{N_M}^{(k)})$ | 1 |
| $(V_1^{(l)}, \cdots, V_{N_M}^{(l)})$ | $-1$ |
| $\vdots$ | $\vdots$ |

| VALUE OF ELECTROMAGNETIC FIELD | UNIT EXPRESSION OF ACTIVE REGION |
|---|---|
| $(V_1^{(k)}, \cdots, V_{N_M}^{(k)})$ | $\overbrace{0010 \cdots 00}^{m}$ |
| $(V_1^{(l)}, \cdots, V_{N_M}^{(l)})$ | $0100 \cdots 00$ |
| ⋮ | ⋮ | ns
SYSTEM AND METHOD FOR PREDICTING INTERNAL CONDITION OF LIVE BODY

BACKGROUND OF THE INVENTION

1. Field of the Invention

The present invention relates generally to a system and method for predicting and expressing an internal condition of a live body on the basis of a distribution of electromagnetic fields on a scalp of the live body.

2. Description of the Related Art

Conventionally, a system for predicting an internal condition of a live body as illustrated in FIG. 16 has been employed for predicting a word to be spoken by a testee. Such system has been disclosed in Japanese Unexamined Patent Publication (Kokai) No. Heisei 2-232783, for example.

In FIG. 16, 91 denotes a plurality of electrodes, 92 denotes an electroencephalograph, 93 denotes a brain wave topographic pattern generator device, 94 denotes a neural network, 95 denotes a syllable data teaching portion, 96 denotes a syllable presenting portion, 97 denotes a control portion controlling respective components, 98 denotes a voice detector devices and 99 a pre-input processing devise.

In such a live body internal condition predicting system, at first, a certain syllable is spoken by the testee. At this time, a potential distribution of brain wave, i.e. the brain wave topographic pattern, is measured by the topographic pattern generator device 93 via the electrodes 91 and the electroencephalograph 92. By repeating the foregoing measurement sequence for a plurality of times, a plurality of training data is generated.

Employing the training data thus generated, a neural network, i.e. neural network 94 in the shown example, learns a relationship between the syllable thought in the brain of the testee, which is input by the syllable data teaching portion 95, and the potential distribution on the scalp. After completion of learning, the measured potential distribution of the brain wave is input to the neural network 94. Thus, it becomes possible to recognize the intended syllable of the testee without requiring the testee to speak. In the conventional method, the waveform of the brain wave is used as the input data. However, it is inherent to detect noise together with syllable pattern due to background brain wave, thermal noise of the measuring equipment, and so forth. Therefore, a long period has heretofore been required in preparatory processing for removing such noise. As a means for removing the noise, it is typical to perform filtering by fast Fourier transformation (FFT) for the measured brain wave data and thereby to remove frequencies other than the signal to be a subject for analysis.

However, in the conventional method, since the brain wave measured on the scalp of the testee is used as the training data, a huge amount of time is required in generation of data when a large amount of training data is to be prepared, to cause substantial load on the testee. On the other hand, when the amount of training data is reduced, reducing load on the testee, the accuracy of learning of the neural network becomes low, increasing a possibility of failure in recognition of the syllable.

In addition, it is required to maintain data of the entire period, in which data measurement is performed, in a frequency analyzing method employing the FFT. Therefore, to store the data of the entire measurement period, a large amount of memory storage capacity is required. In the filtering employing the FFT, a single common frequency is employed for all of the obtained data throughout the entire period. This causes a problem in that, when a low frequency brain wave component is important at one certain timing, and a high frequency brain wave component is important at another timing, one of the two frequency components will be excluded through the filtering.

Also, when the internal condition is to be predicted on the basis of the obtained measured data, it becomes necessary to perform retrieval on a dictionary. The retrieval process requires an additional period.

SUMMARY OF THE INVENTION

The present invention has been worked out for solving the problems set forth above. It is an object of the present invention to provide a system for predicting the internal condition of a live body which can significantly reduce load on a testee, and instantly detects a content of category which the testee wishes to speak.

According to the first aspect of the invention, a system for expressing internal condition of a live body which predicts internal condition of the live body on the basis of an electromagnetic field distribution measured on a scalp of the live body, comprises:

electromagnetic field distribution measuring means for measuring electromagnetic field distribution caused on the scalp of the live body;

training data generating means for generating a plurality of training data on the basis of an electromagnetic field distribution derived from a head model data designating a head model and a predetermined dipole parameter and an internal condition category data describing a relationship between the active region of a brain and the internal condition of the live body;

inferencing means for deriving a numeric value representative of the active region of the brain from the electromagnetic field distribution in the training data with employing a neural network consisted of an input layer, an output layer and at least one hidden layer and having predetermined coupling coefficients representative of coupling condition between each unit forming each layer;

transforming means for transforming the numeric value representative of the active region in the brain output from the inferencing means into an expression indicative of the internal condition of the live body; and the inferencing means having a coupling coefficient modifying means for modifying the coupling coefficient of the neural network for reducing an error between a correct numeric value representative of the correct active region of the brain described in the training data and the numeric value derived by the neural network and indicative of the active region of the brain so that a numeric value indicative of the active region in the brain is derived by the neural network with taking the electromagnetic field distribution measured by the electromagnetic field distribution measuring means when the error becomes smaller than a predetermined reference value.

The live body internal condition expressing system may further comprise noise data adding means for generating a noise and adding the generated noise to the training data generated by the training data generating means.

In the preferred construction, the inferencing means may employ a re-current type neural network.

According to the second aspect of the invention, a method for expressing the live body, in which the internal condition of the live body is predicted on the basis of an electromagnetic field distribution measured on a scalp of the live body, comprises the steps of:

generating a plurality of training data on the basis of an electromagnetic field distribution derived from a head model data designating a head model and a predetermined dipole parameter and an internal condition category data describing a relationship between the active region of a brain and the internal condition of the live body;

deriving a numeric value representative of the active region of the brain from the electromagnetic field distribution in the training data with employing a neural network consisted of an input layer, an output layer and at least one hidden layer and having predetermined coupling coefficients representative of coupling condition between each unit forming each layer;

modifying the coupling coefficient of the neural network for reducing an error between a correct numeric value representative of the correct active region of the brain described in the training data and the numeric value derived by the neural network and indicative of the active region of the brain; and deriving a numeric value indicative of the active region in the brain by the neural network with taking the electromagnetic field distribution measured by the electromagnetic field distribution measuring means when the error becomes smaller than a predetermined reference value.

According to the third aspect of the invention, a system for predicting an internal condition of a live body for predicting the internal condition of the live body on the basis of an electromagnetic field distribution measured on a scalp of the live body, comprises:

electromagnetic field distribution measuring means for measuring an electromagnetic field distribution on the scalp of the live body;

wavelet transforming means for performing wavelet transformation for the electromagnetic field distribution measured by the electromagnetic field distribution measuring means for eliminating a noise component therefrom;

dipole parameter generating means for generating a dipole parameter employing a random number;

training data generating means for generating a plurality of training data on the basis of an electromagnetic field distribution derived from a head model data designating a head model and a predetermined dipole parameter and an internal condition category data describing a relationship between the active region of a brain and the internal condition of the live body;

inferencing means for deriving a numeric value representative of the active region of the brain from the electromagnetic field distribution in the training data with employing a neural network consisted of an input layer, an output layer and at least one hidden layer and having predetermined coupling coefficients representative of coupling condition between each unit forming each layer;

transforming means for transforming the numeric value representative of the active region in the brain output from the inferencing means into an expression indicative of the internal condition of the live body.

Preferably, the inferencing means has coupling coefficient modifying means for modifying the coupling coefficient of the neural network for reducing an error between a correct numeric value representative of the correct active region of the brain described in the training data and the numeric value derived by the neural network and indicative of the active region of the brain so that a numeric value indicative of the active region in the brain is derived by the neural network with taking the electromagnetic field distribution eliminated the noise when the error becomes smaller than a predetermined reference value.

The live body internal condition predicting system may further comprise parameter number modifying portion for varying number of the coupling coefficients and number of the units forming the hidden layer to minimize a description length of the neural network, which description length is derived by dividing a product of a logarithm of number of the training data and number of parameters to be employed in the neural network by two, and multiplying the quotient with a value derived by subtracting one from a maximum logarithm likelihood. In the alternative, the live body internal condition predicting system may further comprise parameter number modifying portion for varying number of the coupling coefficients and number of the units forming the hidden layer to minimize an Akaike's Information Criterion of the neural network, which Akaike's Information Criterion is derived by summing a value derived by multiplying the number of parameters to be employed in the neural network by 2 and a value derived by multiplying the maximum logarithm likelihood by −2.

According to the fourth aspect of the invention, a system for expressing internal condition of a live body which predicts internal condition of the live body on the basis of an electromagnetic field distribution measured on a scalp of the live body, comprises:

electromagnetic field distribution measuring means for measuring electromagnetic field distribution caused on the scalp of the live body;

training data generating means for generating a plurality of training data on the basis of an electromagnetic field distribution derived from a head model data designating a head model and a predetermined dipole parameter and an internal condition category data describing a relationship between the active region of a brain and the internal condition of the live body;

inferencing means for deriving a numeric value representative of the active region of the brain from the electromagnetic field distribution in the training data with employing a neural network consisted of an input layer, an output layer and at least one hidden layer and having predetermined coupling coefficients representative of coupling condition between each unit forming each layer, the inference means deriving a numeric value indicative of the active region in the brain by the neural network with taking the electromagnetic field distribution measured by the electromagnetic field distribution measuring means; and transforming means for transforming the numeric value representative of the active region in the brain output from the inferencing means into an expression indicative of the internal condition of the live body.

Preferably, the neural network in the inferencing means has the coupling coefficients at which an error between a correct numeric value representative of the correct active region of the brain described in the training data and the numeric value derived by the neural network and indicative of the active region of the brain becomes minimum. The inferencing means may have a coupling coefficient modifying means for modifying the coupling coefficient of the neural network for reducing an error between a correct numeric value representative of the correct active region of the brain described in the training data and the numeric value derived by the neural network and indicative of the active region of the brain to be minimum so that the inferencing means derives a numeric value indicative of the active region in the brain by the neural network with taking the electromagnetic field distribution measured by the electromagnetic field distribution measuring means when the error becomes smaller than a predetermined reference value.

The live body internal condition expressing system may further comprise normalizing means for normalizing the training data and the measured value of the electromagnetic field distribution measured by the electromagnetic field distribution measuring means.

The live body internal condition expressing system may further comprise noise eliminating means for eliminating noise component from the measured value of the electromagnetic field distribution measured by the electromagnetic field distribution measuring means. In the preferred construction, the noise eliminating means comprises wavelet transforming means for performing wavelet transformation for removing noise from the measured value of the electromagnetic field distribution measured by the electromagnetic field distribution measuring means.

BRIEF DESCRIPTION OF THE DRAWINGS

The present invention will be understood more fully from the detailed description given herebelow and from the accompanying drawings of the preferred embodiment of the invention, which, however, should not be taken to be limitative to the present invention, but are for explanation and understanding only.

In the drawings:

FIG. 12 is an explanatory illustration showing an internal category data;

FIG. 13 is an explanatory illustration showing a training data;

DESCRIPTION OF THE PREFERRED EMBODIMENT

Figure 1:
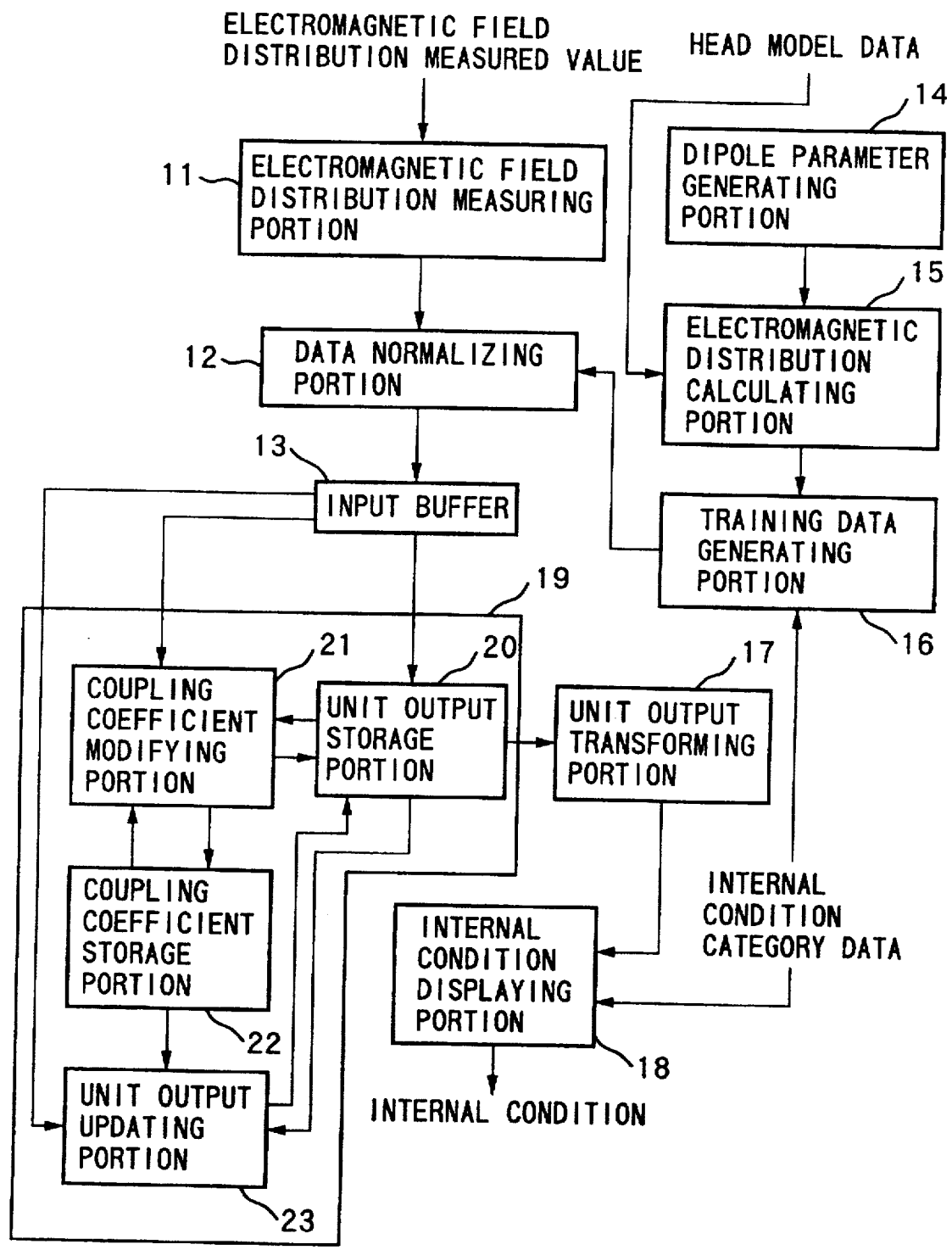
FIG. 1 is a block diagram of the first embodiment of a live body internal condition expressing system according to the present invention.

The present invention will be discussed hereinafter in detail in terms of the preferred embodiments, with reference to the accompanying drawings. In the following description, numerous specific details are set forth in order to provide a thorough understanding of the present invention. It will be obvious, however, to those skilled in the art that the present invention may be practiced without these specific details. In other instances, well-known structures are not shown in detail to avoid obscuring the present invention.

A basic principle of the present invention is to predict an internal condition in a live body on the basis of a distribution of electromagnetic fields on a scalp, by learning a relationship between the electromagnetic field distribution measured on the scalp of the live body and activated area in the brain by a neural network.

In the present invention, learning is performed in a neural network with respect to a relationship between the distribution of the electromagnetic field measured on the scalp and the position of dipole as a source of the distribution of the electromagnetic field. Here, "learning" means modification of a coupling coefficient of the neural network for correctly outputting position of the dipole as the source of the electromagnetic field distribution with respect to the input of the distribution of the electromagnetic field.

On the other hand, it has been known that there is a close relationship between the position of the activated area in the brain and the internal condition of the live body. For example, it is a known fact that when a person is surprised, a characteristic brain wave appears at a point called P300 approximately 300 msec. after presentation of the impulse to be a cause of the surprise. At this moment, the neuron in the deep portion of the brain is activated. Accordingly, by predicting the activity in the brain by the neural network, the internal condition of the live body can be predicted.

Once learning of the neural network is completed, the result of learning is reflected on the coupling coefficient of the neural network. In such a case, arithmetic operation required in actual prediction is only forward calculation for deriving the output of the neural network. Therefore, in the present invention, the internal condition of the live body can be predicted at high speed.

In the present invention, a training data generating portion is provided. The training data generating portion generates a training data employing a model of the head of the live body. Therefore, upon generation of the training data, it becomes unnecessary to measure the distribution of the electromagnetic field at the head of the testee, thus significantly reducing the load on the testee.

Furthermore, in the preferred method, as a frequency analyzing method of the brain wave and the neuro-magnetic-field, wavelet transformation is used. By this, it becomes possible to remove the noise by transformation on the basis of the data of a short period and to make it possible to perform prediction of the internal condition of the live body in the real time.

FIG. 1 is a block diagram showing the first embodiment of a live body internal condition expressing system according to the present invention. In FIG. 1, the reference numeral 11 denotes an electromagnetic field distribution measuring portion measuring distribution of the electromagnetic field generated on the scalp of the live body (testee). 14 denotes a dipole parameter generating portion generating a dipole parameter. 15 denotes an electromagnetic field distribution calculating portion calculating a distribution of the electromagnetic field caused on the scalp on the head model on the basis of the dipole parameter. 16 denotes a training data generating portion generating a training data on the basis of the internal condition category data and a calculated value of the electromagnetic field distribution calculated by the distribution of the electromagnetic field calculating portion 15. 12 denotes a data normalizing portion normalizing the training data from the training data generating portion 16 and the electromagnetic field distribution measured value from an electromagnetic field distribution measuring portion 11. The reference numeral 13 denotes an input buffer for temporarily storing the training data or the electromagnetic field distribution measured value normalized by the normalizing portion 12. 19 denotes a neural network (NN) portion (inferencing means) predicting an active region in the brain on the basis of the electromagnetic field distribution measured value from the input buffer 3 and outputting the predicted value. 18 denotes an internal condition displaying device displaying internal condition category from a unit output converting portion 17.

It should be noted that the dipole parameter generating portion 14, the electromagnetic field calculating portion 15 and the training data generating portion form a training data generating means.

The neural network portion 19 has a neural network constituted of an input layer, an output layer and one or more hidden layers to store the training data and the electromagnetic field distribution calculated value from the input buffer 13. The neural network portion 19 includes a unit output storage portion 20 storing updated unit output, a coupling coefficient storage portion 22 storing the coupling coefficient between respective layers forming the neural network, a coupling coefficient modifying portion 21 (coupling coefficient modifying means) for modifying the coupling coefficient stored in the coupling coefficient storage portion 22 on the basis of the storage content in the input buffer 13 and the unit output storage portion 20, and a unit output updating portion 23 updating the unit output on the basis of the unit output of the unit output storage portion 20 and the coupling coefficient of the coupling coefficient storage portion 22.

Figure 2:
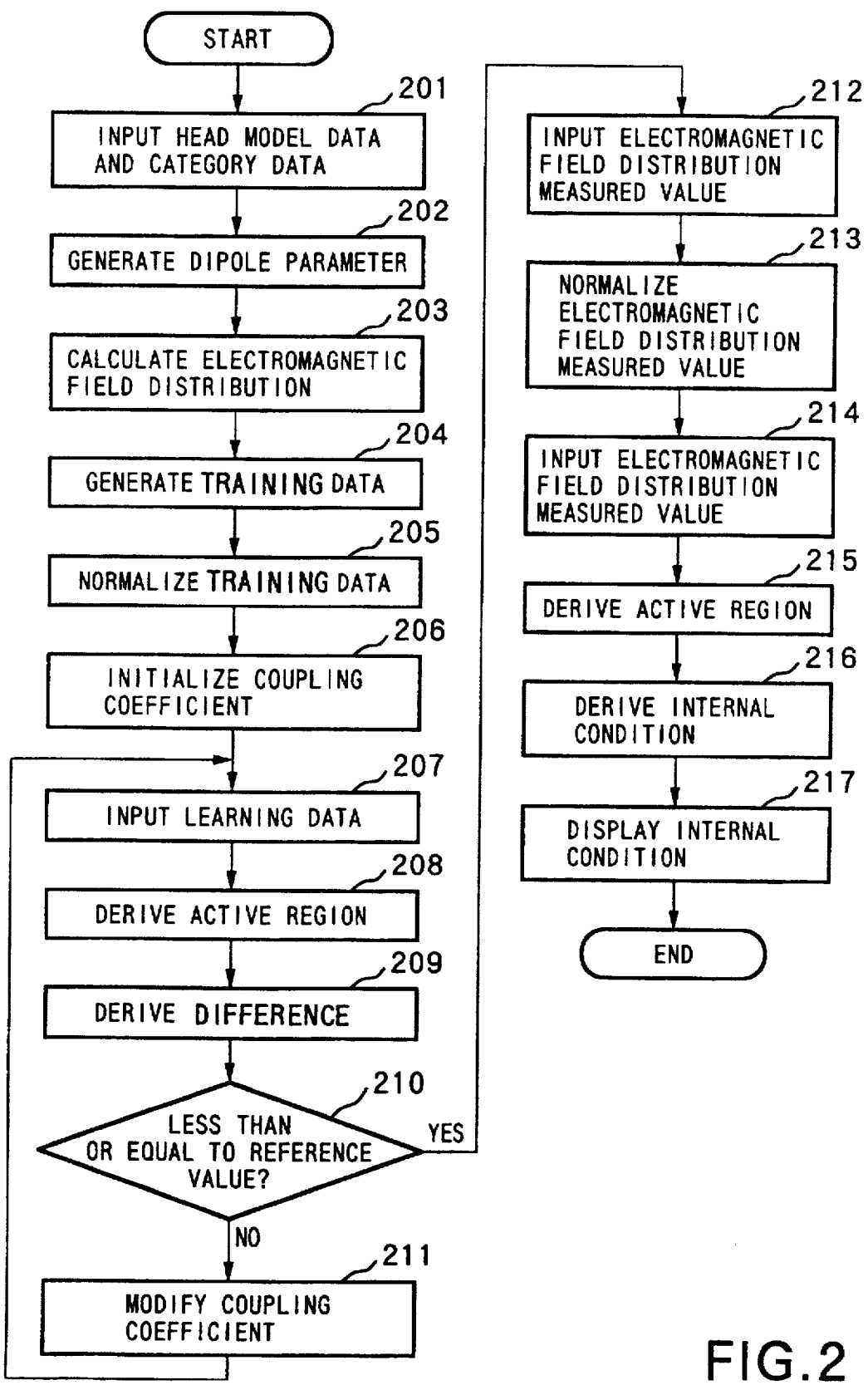
FIG. 2 is a flowchart showing a flow of a live body internal condition expressing process performed in the first embodiment of the live body internal condition expressing system of the present invention.

FIG. 2 is a flowchart showing a flow of process to be performed in the first embodiment of the live body internal condition expressing system according to the present invention. The operation of the first embodiment of the live body internal condition expressing system constructed as set forth above will be discussed with reference to FIGS. 1 and 2.

At a step 201, a head model data is input to the electromagnetic field distribution calculating portion 15, and the internal condition category is input to the training data generating portion 16.

At first, discussion will be given with respect to the head model.

Figure 10:
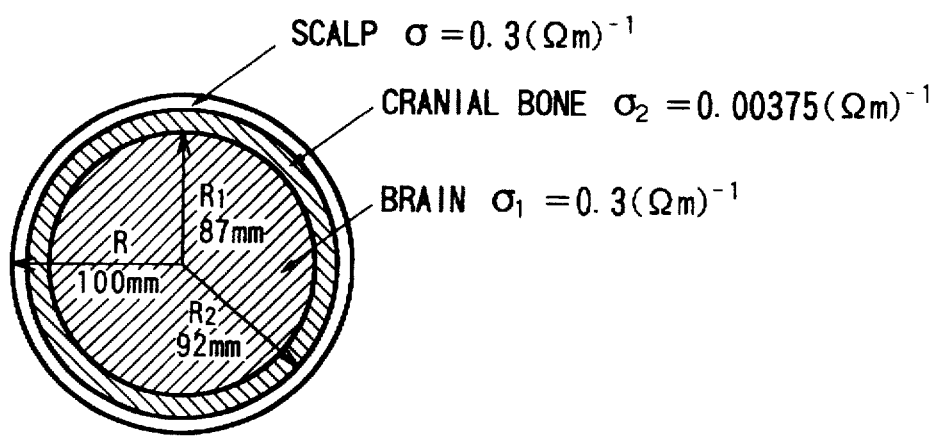
FIG. 10 is an explanatory illustration showing a model of a head.

The head model data is a set of data of a configuration of a head model, a conductivity and coordinates of measuring points on the scalp. When a three layer spherical model shown in FIG. 10 is employed as the head model, the data defining the configuration of the head model consists of numeric values indicative of radius of three spheres corresponding to brain, cranial bones and scalp. Similarly, the conductivity data is consisted of numeric values. The coordinate data of the measuring points is consisted of sets of coordinates of the measuring points set on the head model corresponding to the positions of the electrodes or SQUID magnetic sensors set on the head of the testee upon actual measurement.

Next, discussion will be given for the internal condition category data.

The word "internal condition" represents a state of mind, such as anger, irritation, calmness and so forth. As set forth above, it has been known when a person is surprised, a characteristic brain wave appears at a point called P300 approximately 300 msec. after presentation of the impulse to be a cause of the surprise. At this moment, the neuron in the deep portion of the brain is activated. Therefore, by performing learning of the neural network with respect to the relationship between the brain wave and the active portion in the brain, the internal condition can be predicted. The P300 component has been discussed in detail in C. D. Yingling and Y. Hosobuchi, "A Subcortical Correlate of P300 in Man", Electroencephalography and Clinical Neurophysiology, 1984, Vol. 59, pp 72 to 76.

Figure 11:
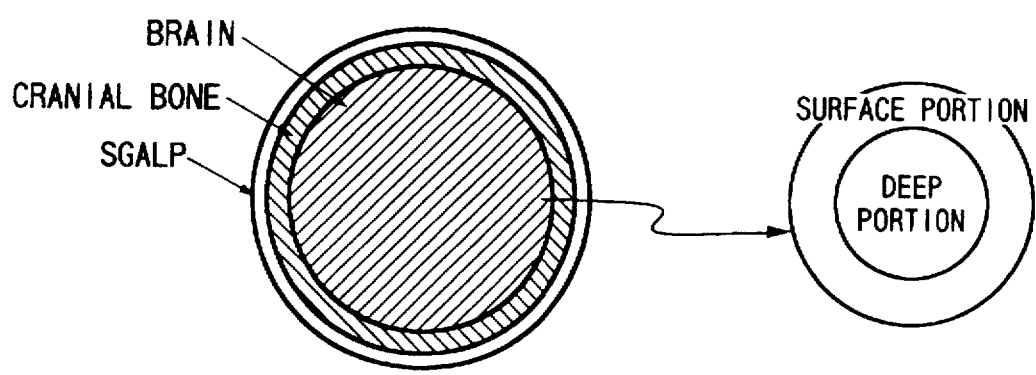
FIG. 11 is an explanatory illustration illustrating a manner of division of a brain into a plurality of regions.

The internal condition category data is generated in the following manner in advance of learning. At first, the portion corresponding to the brain in the head model is divided into a plurality of regions. In the shown example, discussion will be given in the case where the brain portion is divided into a deep portion and surface portion as illustrated in FIG. 11. When the brain portion is to be divided into three or more portions, it can be done in the similar dimension. Two regions are expressed employing Cartesian coordinate system or polar coordinates system. For respective regions, numeric value and the internal condition are assigned. FIG. 12 shows an example of the internal condition category data in the case the divided regions in the brain of the head model are expressed by employing the polar coordinates. It should be noted that, in FIG. 12, $R_b$ is a radius of the sphere corresponding to the brain and the numeric data is used as a target output of learning of the neural network.

At a step 202, a dipole parameter which is necessary for calculation of the electromagnetic field data as the input signal of the training data of the neural network, is generated by the dipole parameter generating portion 5. The dipole parameter is consisted of a set of a three components (x, y, z) of the position of the dipole and moment vectors ($M_x$, $M_y$, $M_z$). The dipole parameter generating portion 5 generates $N_t$ sets of dipole parameters using a random number. Here, $N_t$ is a number of the training data which is normally set in a range of 5000 to 10000. In generation of the dipole parameter, the following constraints may be provided.

$$\sqrt{x^2 + y^2 + z^2} \leq R_b \tag{1}$$

$$\sqrt{M_x^2 + M_y^2 + M_z^2} \leq \mu \tag{2}$$

wherein μ is a maximum value of the moment vector, which is determined so that the electromagnetic field measured on the scalp and the electromagnetic field calculated on the basis of the dipole parameter becomes substantially equal to each other. $N_t$ in number of dipole parameters generated in the dipole parameter generating portion 14 is fed to the electromagnetic field distribution calculating portion 15 and thus used for calculation of the electromagnetic field distribution.

The dipole parameter generating portion 14 can be realized by employing a personal computer or an engineering work station.

At a step 203, the electromagnetic field distribution is calculated by the electromagnetic field distribution calculating portion 15 on the basis of the dipole parameter generated at the step 202. Calculation of the electromagnetic field distribution on the basis of the dipole parameter is performed in the following manner.

In the following discussion, assuming that three layer conductive sphere having the radius R and uniform conductivity as the head model, method for discussing the potential to be generated on the surface of the conductive sphere is discussed. A coordinate system is established with taking the center of the conductive sphere as origin. Then, when a dipole having a moment components on the z-axis at a position ($M_r$, O, $M_t$) in a distance r from the origin is present, a potential V generated at a point on the spherical surface at the position (R, θ, φ) can be expressed as follow:

$$V(R, \theta, \phi) = \qquad (3)$$

$$\sum_{n=1}^{m} \frac{1}{4\pi\sigma R^2} \frac{2n-1}{n} \left(\frac{\gamma}{R}\right)^{n-1} [nM_r Y_{n0}^0(\theta,\phi) + M_t Y_{n0}^1(\theta,\phi)]$$

wherein σ is a conductivity of sphere and $Y_{n\alpha}^m(\theta, \psi)$ is a spherical harmonics expressed by:

$$Y_{n\alpha}^m(\theta,\phi) = \qquad (4)$$

$$\sqrt{\frac{2n+1}{2n} \frac{1}{1+\delta_{0m}} \frac{(n-m)!}{(n+m)!}} P_n^m(\cos\theta) \times \begin{cases} \cos m\phi\alpha = 0 \\ \sin m\phi\alpha = 1 \end{cases}$$

$P_n^m$ (x) is a associated Legendre function, $\delta_{ij}$ is a Kronecker delta defined by:

$$\delta_{ij} = \begin{cases} 1 & i=j \\ 0 & i \neq j \end{cases} \qquad (5)$$

The equation (3) expresses the potential in the case where the dipole is present on the z-axis and thus the y component of the moment is zero. For the dipole at the arbitrary position, the potential may be derived from the foregoing equation (3) through coordinate conversion. When a plurality of dipoles are present, the potentials generated by respective dipoles are simply summed to derive the potential generated at a point on the spherical surface at the position (R, θ, φ).

The electromagnetic field distribution calculating portion 15 feeds a set of the dipole parameter $p^{(i)}$ and the electromagnetic field component $V^{(i)}$ calculated utilizing the dipole parameter $p^{(i)}$ with respect to $N_M$ in number of points on the head model, in which the dipole parameter $p^{(i)}$ is expressed by:

$p^{(i)}=(x^{(i)}, y^{(i)}, z^{(i)}, M_x^{(i)}, M_y^{(i)}, M_z^{(i)})$, (i=1, . . . $N_t$)

and $V^{(i)}$ is expressed by:

$V^{(i)}=(V_1^{(i)}, \ldots, V_{Nm}^{(i)})$ (i=1, . . . , $N_t$)

The electromagnetic field distribution calculating portion 15 can be realized by a personal computer, engineering work station or so forth.

The calculation method of the head model and the electromagnetic field distribution has been discussed in detail in James P. Ary, et al. "Location of Sources of Evoked Scalp Potentials: Correactions for Skill and Scalp Thickness", IEEE Translations of Biomedical Engineering, Vol. BME-28, No. 6, June 1981.

It should be noted that while the shown embodiment has been discussed in terms of calculation method for electric field (potential) among the electromagnetic field data on the scalp, the method may be implemented by utilizing distribution of the magnetic field expressed by:

$$B(r) = \frac{\mu_0}{4\pi} \int_V M(r') \times \nabla' \left(\frac{1}{|r-r'|}\right) d^3r'$$

wherein M(r') is the dipole generated at the position r', x is the coordinates of the measuring position of the magnetic field.

At a step 204, the training data is generated by the training data generating portion 16. The training data generating portion 16 receives the set of the dipole parameter and the electromagnetic field distribution from the electromagnetic field distribution calculating portion 15 and preliminarily prepared internal condition category data and generates the training data for the neural network. Accordingly, the training data is a set of the values of the electromagnetic fields at $N_m$ in number of points on the scalp and a value representative of the active region in the brain. For example, when the electromagnetic field data $V^{(k)}$ is caused by the dipole placed on the inner region among two regions of the head model sphere, expressed by:

$$p^{(k)} = (x^{(k)}, y^{(k)}, z^{(k)}, M_x^{(k)}, M_y^{(k)}, M_z^{(k)}), \sqrt{(x^{(k)2} + y^{(k)2} + z^{(k)2}}} \leq \frac{R_b}{2}$$

then, the numerical expression of the active region in the brain becomes −1, and when the electromagnetic field data $V^{(1)}$ is caused by the dipole placed on the outer region among two regions of the head model sphere, expressed by:

$$p^{(1)} = (x^{(1)}, y^{(1)}, z^{(1)}, M_x^{(1)}, M_y^{(1)}, M_z^{(1)}), \sqrt{(x^{(1)2} + y^{(1)2} + z^{(1)2}}} > \frac{R_b}{2}$$

then, the numerical expression of the active region in the brain becomes 1.

The numerical expression of the active region in the brain generated through the process set forth above is utilized as the training data.

The training data generating portion 16 may be realized by employing the personal computer, engineering work station and so forth.

At a step 205, the training data is normalized by the data normalizing portion 12. Normalization of the training data is performed through the following process. Assuming that the calculated value of the electromagnetic field distribution data at the first measuring point is $V_1$ and the normalized electromagnetic field distribution data is $V_1'$, then the normalized electromagnetic field distribution data can be expressed by:

$$V_i' = a \times \frac{V_i}{\max|V_i|}$$

wherein max|V| represents the maximum value of the electromagnetic value among all training data, a is a normalization constant which is optimal at 0.8 but can be of any other positive value. Since excessively large value of the input data makes learning difficult, normalization of the input value is performed for limiting the maximum value of the input value to make learning efficient. The formula to perform normalization is not limited to the foregoing equation but can be any appropriate formulae deriving the value less than or equal to 1. The normalized data by the data normalizing portion 12 is fed to the input buffer 13 and held therein.

The data normalizing portion 12 can be realized by employing the personal computer, the engineering work station and so forth. Also, the input buffer 13 may be realized by employing a magnetic disk drive, a semiconductor memory device, a magneto-optical disk drive and so forth.

At a step 206, the coupling coefficients of the neural network stored in the coupling coefficient storage portion 22 are initialized by employing a random number or the like so forth. The coupling coefficient storage portion 22 may be realized by a magnetic disk drive, a semiconductor memory device, a magneto-optical disk drive and so forth.

At a step 207, the electromagnetic field distribution of the training data is input to the input layer of the neural network forming the unit output storage portion 20. The unit output storage portion 20 may be realized by a neuro board, such as Neuro-07(tradename), NEC Corporation, a magnetic disk drive, a semiconductor memory device, a magneto-optical disk drive and so forth.

Figure 8:
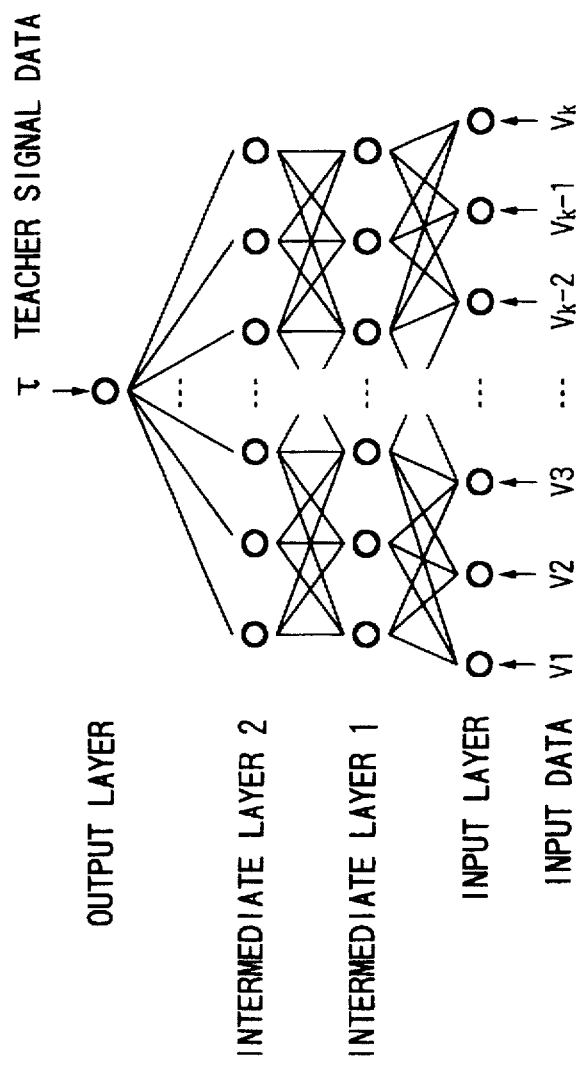
FIG. 8 is an explanatory illustration showing an example of construction of a neural network to be employed in the live body internal condition expressing system of the present invention.

At a step 208, the internal condition is derived by employing the neural network. As generally shown in FIG. 8, the neural network is constructed with three layers respectively called as input layer, output layers and one or more hidden layer. Also, in each layer of the neural network, process unit system (shown by 0 in FIG. 9) called as unit are arranged. Each unit receives input from the adjacent unit or units at the input side and feeds the output to the adjacent unit at the output side. The input/out relationship of respective units are calculated in the unit output updating portion 23, and can be defined as follow:

$$h_i^{(l)} = \sum_j W_{ij}^{(l)} v_j^{(l-1)} + \theta_i^{(l)} \quad (6)$$

$$v_i(l) = g(h_i^{(l)}) \quad (7)$$

$$g(x) = \frac{1}{1+e^{-x}} \quad (8)$$

wherein h is representative of the input to the unit, v is representative of the output of the unit, θ is indicative of a threshold value of the unit. The superscript suffix represents the number of layers counted from the input layer, and the subscript suffix represents number of the unit in the layer. On the other hand, $W_{ij}$ represents the coupling coefficient between the (j)th unit in the (l−1) layer and (i)th unit in the first layer. g(x) is a response function of input and output. Thus, by calculation from the input layer to the output layer in order, the output can be finally obtained from the output layer. The output thus obtained is the dipole parameter derived by the neural network system. As the response function, tan h(x) may be employed in place of the foregoing equation (8), and any other appropriate function may also be employed.

At a step 209, a difference between the dipole parameter derived by the neural network system and the dipole parameter in the training data is calculated. In the following discussion, the difference thus obtained will be referred to as error E. The error E is defined by employing square error, as:

$$E = \frac{1}{2} \sum_i (o_i - \tau_i)^2 \quad (9)$$

wherein $o_i$ is an output from the first unit in the output layer, $\tau_i$ is the correct output of the corresponding unit. The error E is not necessarily the square error but can be of any non-negative function which becomes zero when all of $o_i$ and $\tau_i$ are coincident to each other. In the following discussion, the correct output of the neural network will be referred to as "target output".

At a step 210, check is performed whether the error E is less than or equal to a preliminarily set reference value. When the error E is less than or equal to the reference value, the process is advanced to a step 212. On the other hand, when the error E is greater than the reference value, the process is advanced to a step 211, in which the coupling coefficient is modified by the coupling coefficient modifying portion 21 to make the error E smaller. As a method for modifying the coupling coefficient, an error back propagation method and so forth may be employed. The concrete method of modification employing the error back propagation method has been discussed in detail in D. E. Rumelhart et al, "Parallel Distributed Processing", Vol. 1, MIT Press, pp 318 to 362, 1986.

At the step 212, by employing the electromagnetic field distribution measuring portion 11, the values of the electromagnetic field distribution at respective points on the scalp are measured. Then, at a step 213, the values of the electromagnetic field distribution as input from the electromagnetic field distribution measuring portion 11 are normalized by the data normalizing portion 12. The normalized data is then fed to the input buffer 13 and held therein. It should be noted that the normalization is performed in the similar manner to that discussed with respect to the step 205.

At a step 214, the normalized measured value of the electromagnetic field distribution held in the input buffer 13 is fed to the input layer of the neural network.

At a step 215, the active region in the brain is derived from the measured value of the electromagnetic field employing the neural network. The process of the arithmetic operation for deriving the active region in the brain is similar to that discussed with respect to the step 208. At a step 216, on the basis of the preliminarily prepared internal condition category, the active region in the brain as derived by utilizing the neural network is converted into the expression representative of the internal condition. Then, the converted data indicative of the internal condition is fed to an internal condition displaying device 18.

At a step 217, the data indicative of the internal condition is transferred to the unit output converting portion 17. Then, the internal condition is displayed and then the process ends.

It should be noted that when learning of the neural network is preliminarily completed and appropriate coupling coefficients are stored in the storage device, such as a hard disk drive or so forth, the process through the steps 202 to 211 may be neglected. Accordingly, once learning is completed, prediction of the internal condition can be performed by merely calculating the output of the neural network. Therefore, a high speed internal condition prediction system can be realized.

Figures 14, 15:
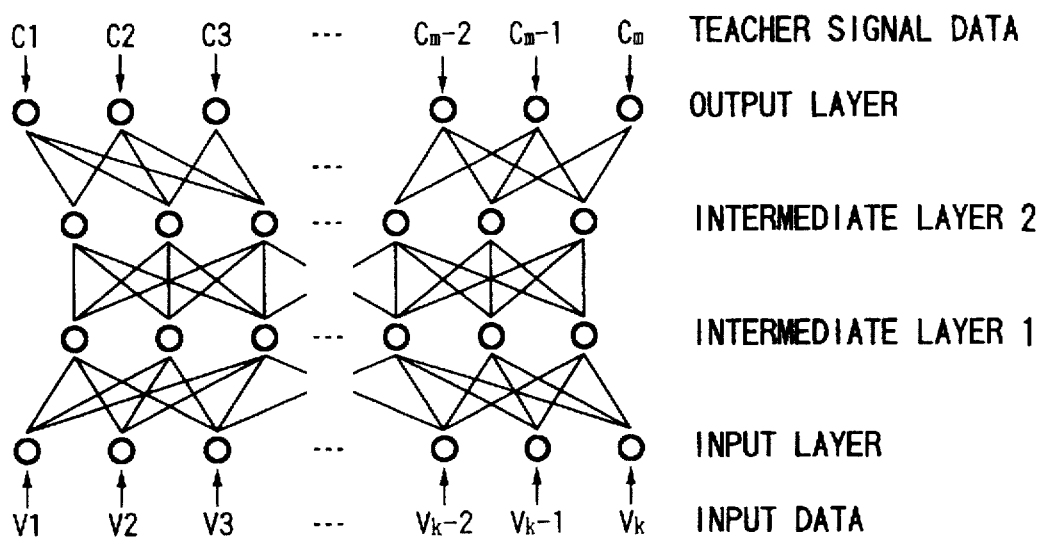
FIG. 14 is an explanatory illustration showing an a further example of construction of a neural network.
FIG. 15 is an explanatory illustration showing a training data corresponding to the neural network illustrated in FIG. 14.
Figure 16:
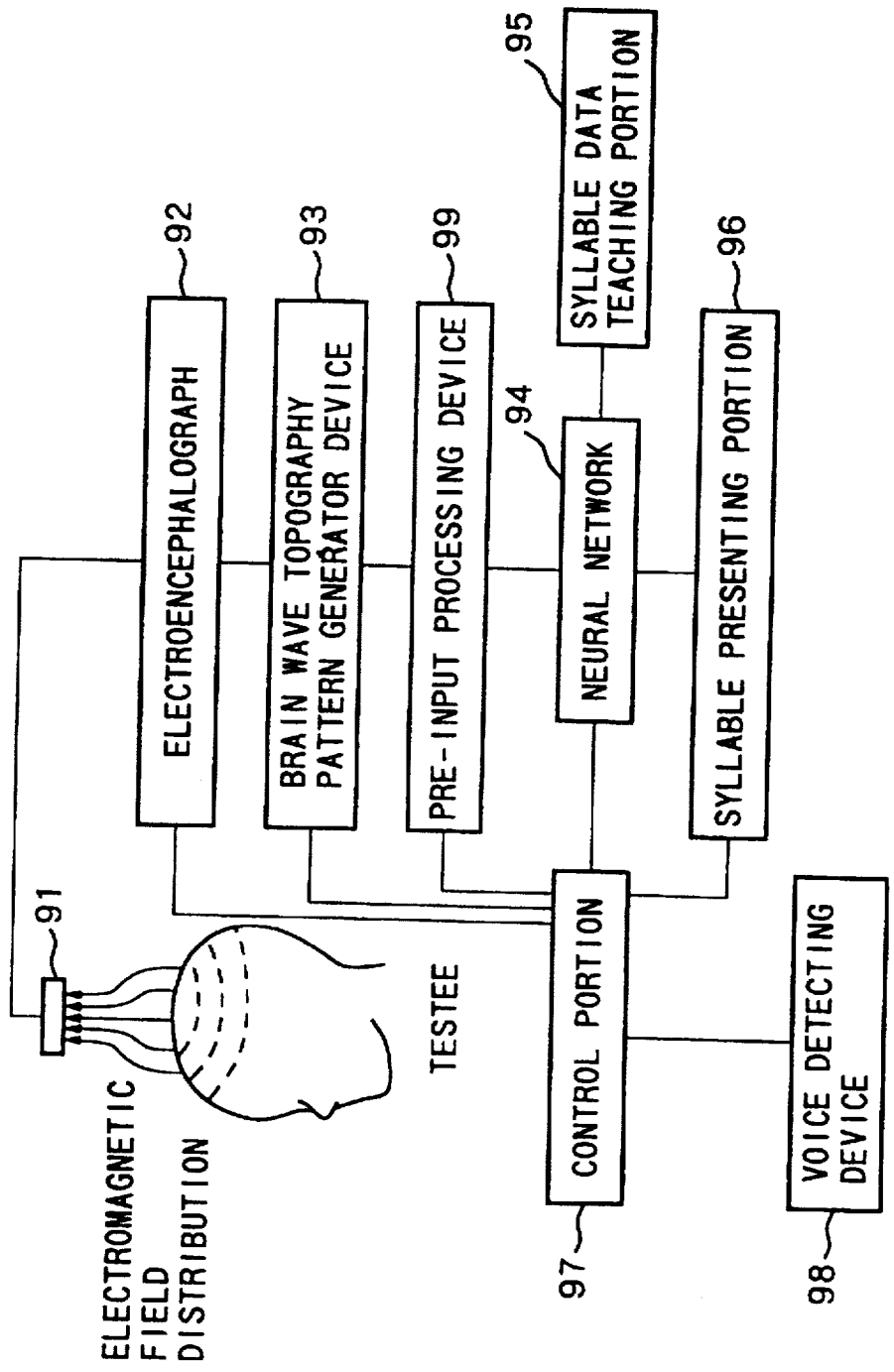
FIG. 16 is an explanatory illustration showing the conventional live body internal condition expressing system.

Also, it should be noted that while the foregoing discussion has been given for the case where the active region in the brain is provided in a form of numeric value as the training data, it is possible to prepare the units in the output layer in number corresponding to the number of categories and to set the unit corresponding to the predicted internal condition to 1 and set remaining unit to 0 to express the internal condition, for example. FIG. 14 is an explanatory illustration showing the construction of the neural network and FIG. 15 is an explanatory illustration of the training data to be input to the neural network. Assuming that there are active regions $C_1, C_2, \ldots, C_m$ of brain divided into m in number of regions, among the unit expression shown in FIG. 15, the units corresponding to the predicted internal condition category become 1 and other units become 0.

Figure 3:
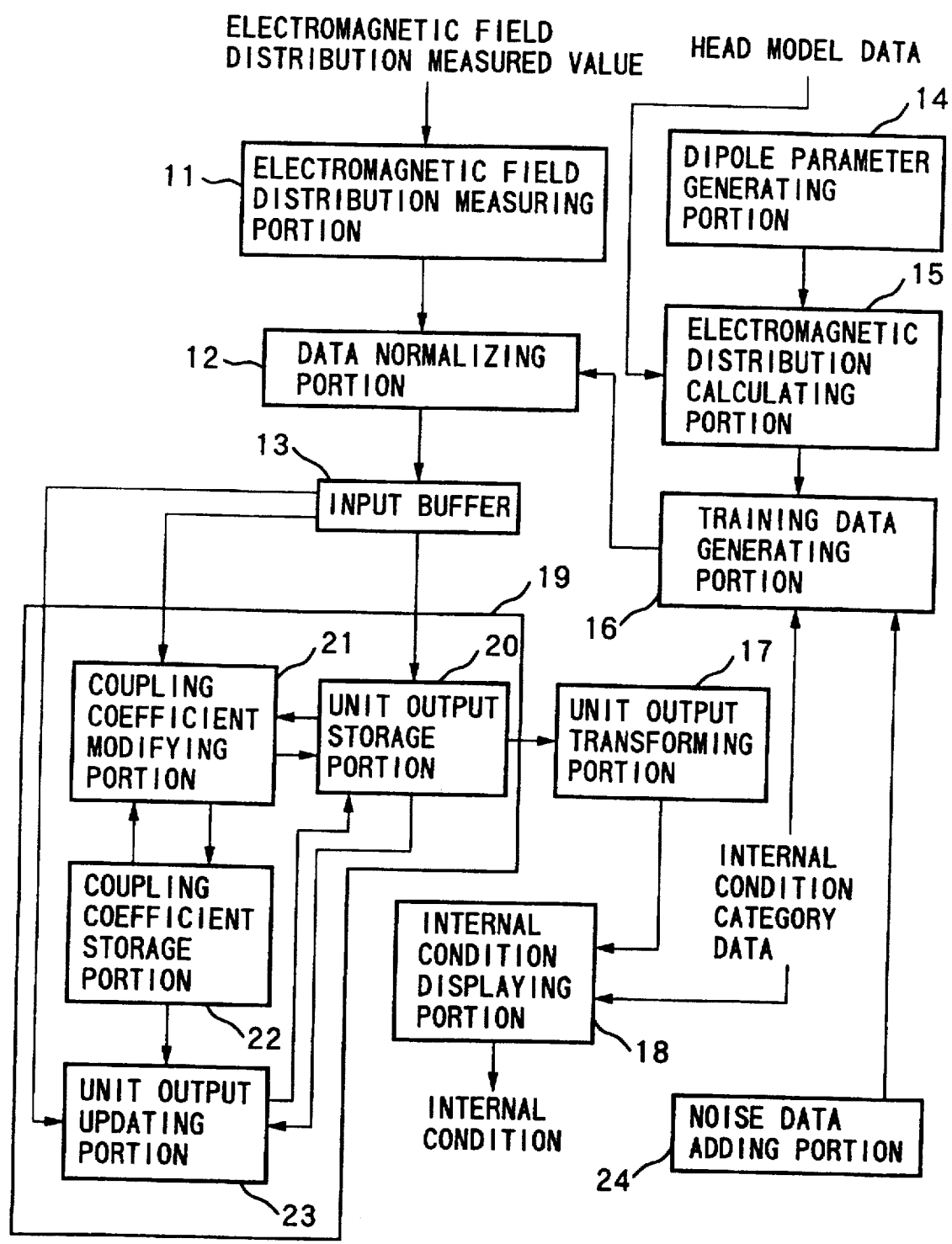
FIG. 3 is a block diagram of the second embodiment of a live body internal condition expressing system according to the present invention.

Next, the second embodiment of the live body internal condition expressing system according to the present invention will be discussed with reference to FIG. 3. In FIG. 3, like reference numerals to FIG. 1 represent like elements. The reference numeral 24 denotes a noise data adding portion generating a noise data and outputting the generated noise data to the training data generating portion 16.

In contrast to the first embodiment set forth above, in which the calculated value of the electromagnetic field distribution to be used as the training data is used as is, it may be possible to use the value indicative of the electromagnetic field distribution, to which a noise component is added.

The noise data adding portion 24 generates the noise component and adds the noise component to the electromagnetic field distribution in the training data generated by the training data generating portion 16.

The electromagnetic field distribution $V_i^{(L)}$ added to the noise component may be expressed by the following equation (10):

$$V_i^{(L)'} = V_i^{(L)} + \eta_i \quad (10)$$

wherein $V_i^{(L)}$ is the calculated value of the electromagnetic distribution point at the first measuring point, $\eta_i$ is the noise component added to the electromagnetic distribution, which noise component may be provided utilizing the random number. Experimentarily, it has been found that the noise component contained in the measured electromagnetic field distribution is in a range of 1/5 to 1/20 of the measured value. Therefore, the random number may be set within this range. On the other hand, the superscript suffix L represents that the electromagnetic distribution is used in the training data.

As can be appreciated, since the electromagnetic field distribution as measured on the scalp may naturally contain a noise component, it becomes possible to realize the live body internal condition expressing system resistive against the noise by making the neural network to preliminarily learn the data containing noise component.

Figure 4:
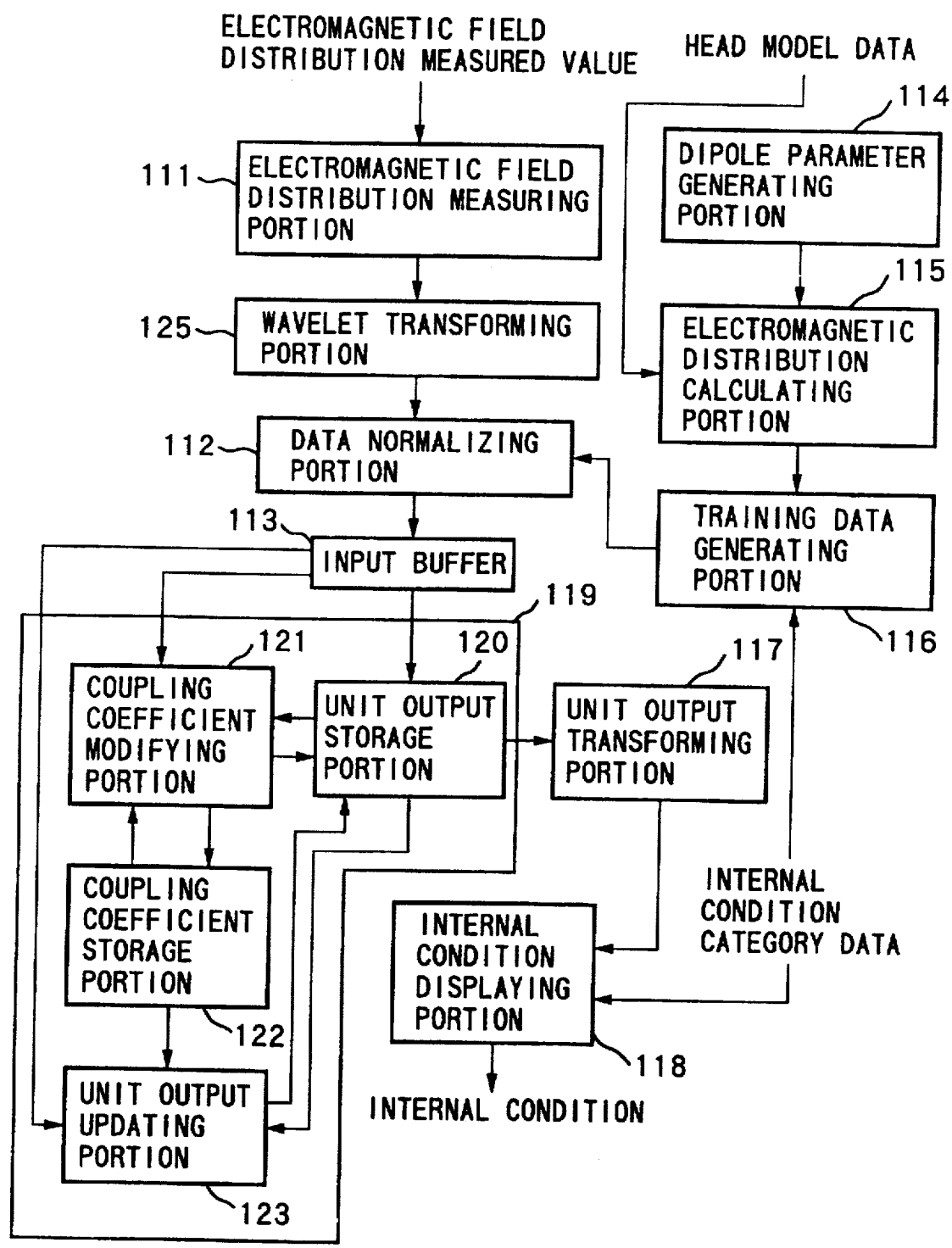
FIG. 4 is a block diagram of the third embodiment of the live body internal condition expressing system according to the present invention.

FIG. 4 shows the third embodiment of the live body internal condition expressing system according to the present invention. In FIG. 4, the reference numeral 111 denotes an electromagnetic field distribution measuring portion similar to the electromagnetic field distribution measuring portion 11 in the former embodiment, 125 denotes a wavelet transforming portion performing wavelet transformation for the electromagnetic field data measured by the electromagnetic field distribution measuring portion 111, 114 denotes a dipole parameter generating portion similar to the dipole parameter generating portion 14 of the former embodiment, 115 denotes an electromagnetic field distribution calculating portion similar to the electromagnetic field distribution calculating portion 115 of the former embodiment, 116 denotes a training data generating portion similar to the training data generating portion 15 of the former embodiment, 112 denotes a data normalizing portion normalizing the electromagnetic field data converted by the wavelet transforming portion 125 and the training data from the training data generating portion 116.

The reference numeral 113 denotes an input buffer for temporarily storing the electromagnetic field data and/or the training data, 120 denotes a unit output storage portion storing the unit output of the neural network, 121 denotes a coupling coefficient modifying portion for modifying the coupling coefficient of the neural network, 119 denotes the neural network (NN) portion (inferencing means) predicting an active region in the brain on the basis of the electromagnetic field data wavelet converted by the wavelet transforming portion 125 and input from the input buffer 13, and output the predicted value, 118 denotes an internal condition displaying device similar to the internal condition displaying device 18 of the former embodiment. It should be noted that the dipole parameter generating portion 114, the electromagnetic field calculating portion 115 and the training data generating portion 116 form a training data generating means.

The neural network portion 119 has a neural network constituted of an input layer, an output layer and one or more hidden layers similar to the former embodiment, and includes the unit output storage portion 120 storing the training data and the electromagnetic field distribution indicative value from the input buffer 113 and further storing updated unit output, a coupling coefficient storage portion 122, the coupling coefficient modifying portion 121 and a unit output updating portion 123 similar to the coupling coefficient storage portion 22, the coupling coefficient modifying portion 21 and the unit output updating portion 23 of the former embodiment.

Figure 5:
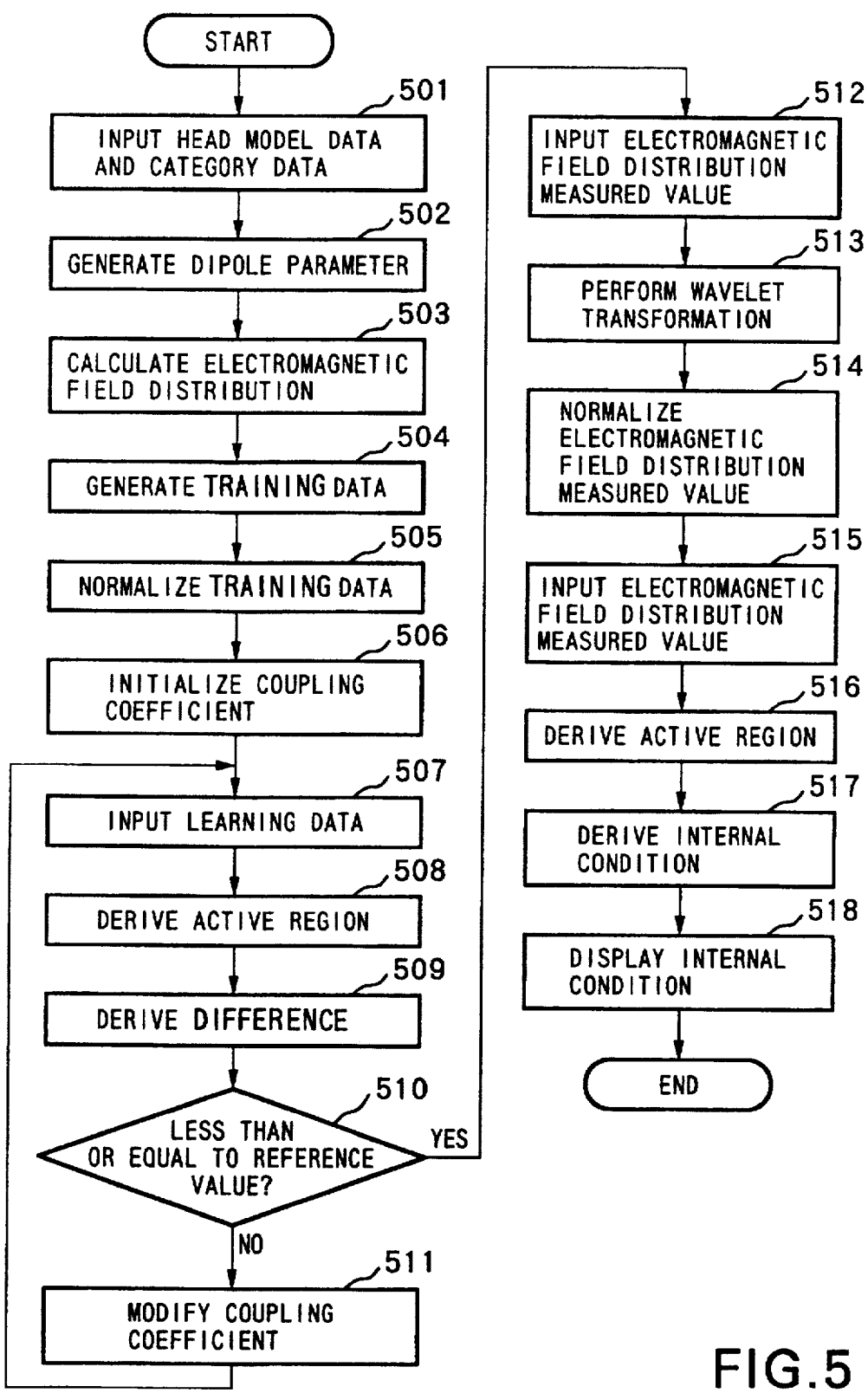
FIG. 5 is a flowchart showing a flow of a live body internal condition expressing process performed in the third embodiment of the live body internal condition expressing system of the present invention.

The operation of the third embodiment of the live body internal condition expressing system according to the present invention will be discussed hereinafter with reference to FIG. 5.

At a step 502, a dipole parameter which is necessary for calculation of the electromagnetic field data as the input signal of the training data of the neural network, is generated by the dipole parameter generating portion 114. The dipole parameter is consisted of a set of a three components (x, y, z) of the position of the dipole and moment vectors ($M_x$, $M_y$, $M_z$). The dipole parameter generating portion 114 generates $N_t$ sets of dipole parameters using a random number. The dipole parameter thus generated is fed to the electromagnetic field distribution calculating portion 115 to be used for calculation of the electromagnetic field distribution.

It should be noted that the constraint is given for the dipole parameter determined by the dipole parameter generating portion similarly to the former embodiment.

At a step 503, the electromagnetic field distribution is calculated by the electromagnetic field distribution calculating portion 115 on the basis of the dipole parameter generated at the step 502. Calculation of the electromagnetic field distribution is performed in the manner similar to the former embodiment.

At a step 504, the training data is generated by the training data generating portion 116. The training data generating portion 116 receives the set of the dipole parameter and the electromagnetic field distribution from the electromagnetic field distribution calculating portion 115 and preliminarily prepared internal condition category data and generates the training data for the neural network. Accordingly, the training data is a set of the values of the electromagnetic fields at $N_m$ in number of points on the scalp and a value representative of the active region in the brain.

At a step 505, the training data is normalized by the data normalizing portion 112. Normalization of the training data is performed through the process similar to the former embodiment.

At a step 506, the coupling coefficients of the neural network stored in the coupling coefficient storage portion 22 is initialized by employing a random number or so forth. The coupling coefficient storage portion 22 may be realized by employ a magnetic disk drive, a semiconductor memory device, a magneto-optical disk drive and so forth.

At a step 507, the electromagnetic field distribution of the training data is input to the input layer of the neural network forming the unit output storage portion 20. The unit output storage portion 20 may be realized by employ a magnetic disk drive, a semiconductor memory device, a magneto-optical disk drive and so forth.

At a step 508, the internal condition is derived by employing the neural network. As generally shown in FIG. 8, the neural network is constructed with three layers respectively called as input layer, output layer and one or more hidden layer. Also, in each layer of the neural network, process unit system (shown by ○ in FIG. 9) called as unit are arranged. Each unit receives input from the adjacent unit or units at the input side and feeds the output to the adjacent unit at the output side. The input/our relationship of respective units are calculated in the manner similar to the former embodiment.

At a step 509, a difference between the dipole parameter derived by the neural network system and the dipole parameter in the training data is calculated. In the following discussion, the difference thus obtained will be referred to as error E. The error E is determined similar to the former embodiment.

At a step 510, check is performed whether the error E is less than or equal to a preliminarily set reference value. When the error E is less than or equal to the reference value, the process is advanced to a step 512. On the other hand, when the error E is greater than the reference value, the process is advanced to a step 511, in which the coupling coefficient is modified by the coupling coefficient modifying portion 121 to make the error E smaller. As a method for modifying the coupling coefficient, an error back propagation method and so forth may be employed.

At the step 512, by employing the electromagnetic field distribution measuring portion 111, the values of the electromagnetic field distribution at respective points on the scalp are measured.

At a step 513, wavelet transformation is performed for the waveform of the measured electromagnetic field to remove the noise component containing in the measured value. Then, the converted data is fed to the data normalizing portion 112. The wavelet transformation per se is known technology. For example, the wavelet transformation technology has been discussed in detail in Charles K. Chui, "An Introduction to Wavelets" Academic Press, 1982. Here, the method of the wavelet transformation will be discussed in more detail. Assuming the value of the waveform calculated at a timing t is expressed as x(t), and unfolding coefficient α(a, b) of the wavelet transformation with respect to the waveform x(t) is:

$$\alpha(a, b) = \int_{-\infty}^{\infty} x(t)\, \psi_{ab}(t)\, dt$$

wherein $$\psi_{ab}(t) = a^{-\frac{1}{2}} \psi\left(\frac{t-b}{a}\right) \quad (11)$$

ψ(t) is called as basic wavelet and basal function for unfolding. The basic wavelet is localized in the region centered at the origin, and the Fourier components also localized with a certain width about one point on the frequency space. The parameter a designates expansion and contraction in the time axis direction of the basic wave function and thus corresponds to the frequency of the Fourier's transformation. The parameter b does not correspond to Fourier's transformation and designates a parallel shifting in the direction of the time axis.

For instance, in certain case, it is possible that the high frequency component of the signal is important for the waveform around a timing $t_1$ and the low frequency component is important and the high frequency component is regarded as noise around a timing $t_2$. When filtering by Fourier conversion of the data is performed by removing the noise of the high frequency component, the information near the timing $t_1$ may be lost.

In contrast to this, in filtering by wavelet transformation, filtering can be performed at different frequency bands at different times, and important signals may be preserved. Therefore, noise can be efficiently removed. Filtering employing the wavelet transformation has been discussed in detail in Olivier Bertrand et al., "Time-Frequency Digital Filtering Based on an Insertible Wavelet Transform: An Application to Evoked Potentials, IEEE Transactions on Biomedical Engineering, Vol. 41, No. 1, January, 1984.

At a step 514, the values of the electromagnetic field distribution as input from the electromagnetic field distribution measuring portion 111 are normalized by the data normalizing portion 112. The normalized data is then fed to the input buffer 113 and held therein. It should be noted that the normalization is performed in the similar manner to that discussed with respect to the step 505.

At a step 515, the normalized measured value of the electromagnetic field distribution held in the input buffer 113 is fed to the input layer of the neural network.

At a step 516, the active region in the brain is derived from the measured value of the electromagnetic field employing the neural network. The process of the arithmetic operation for deriving the active region in the brain is similar to that discussed with respect to the step 508. At a step 517, on the basis of the preliminarily prepared internal condition category, the active region in the brain as derived by utilizing the neural network is converted into the expression representative of the internal condition. Then, the converted data indicative of the internal condition is fed to an internal condition displaying device 118.

At a step 518, the data indicative of the internal condition is transferred to the unit output converting portion 117. Then, the internal condition is displayed and then the process is goes end.

It should be noted that when learning of the neural network is preliminarily completed and appropriate coupling coefficients are stored in the storage device, such as a hard disk drive or so forth, the processed through the steps 502 to 511 may be neglected. Accordingly, once learning is completed, prediction of the internal condition can be performed by merely calculating the output of the neural network. Therefore, a high speed internal condition prediction system can be realized.

Also, it should be noted that while the foregoing discussion has been given for the case where the active region in the brain is provided in a form of numeric value as the training data, it is possible to prepare the units in the output layer in number corresponding to the number of categories and to set the unit corresponding to the predicted internal condition to 1 and set remaining unit to 0 to express the internal condition, for example. FIG. 14 is an explanatory illustration showing the construction of the neural network and FIG. 15 is an explanatory illustration of the training data to be input to the neural network. Assuming that there are active regions $C_1, C_2, \ldots, C_m$ of brain divided into m in number of regions, among the unit expression shown in FIG. 15, the units corresponding to the predicted internal condition category become 1 and other units become 0.

Next, the fourth embodiment of the live body internal condition expressing system according to the present invention will be discussed with reference to FIG. 6. In the following discussion, like reference numerals to the third embodiment of FIG. 4 represent like elements. Detailed description for the overlapping element to the foregoing third embodiment will be neglected from the following discussion.

Figure 6:
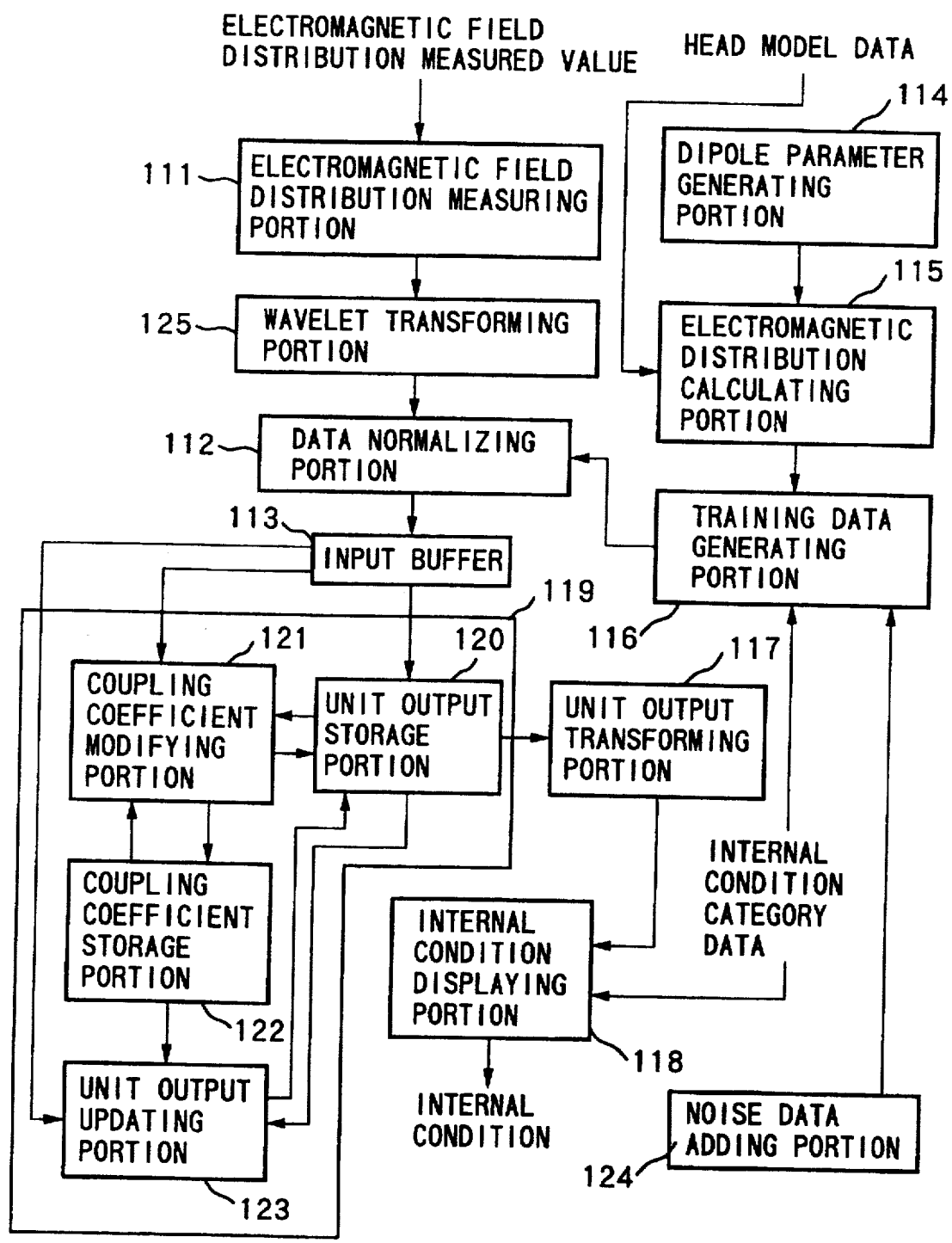
FIG. 6 is a block diagram of the fourth embodiment of a live body internal condition expressing system according to the present invention.

FIG. 6 is a block diagram showing the construction of the fourth embodiment of the live body internal condition expressing system according to the present invention. In FIG. 6, The reference numeral 124 denotes a noise data adding portion generating a noise data and outputting the generated noise data to the training data generating portion 116.

In contrast to the first embodiment set forth above, in which the calculated value of the electromagnetic field distribution to be used as the training data is used as is, it may be possible to use the value indicative of the electromagnetic field distribution, to which a noise component is added.

The noise data adding portion 124 generates the noise component and add the noise component to the electromagnetic field distribution in the training data generated by the training data generating portion 116.

The electromagnetic field distribution $V_i^{(L)}$ added the noise component may be expressed by the following equation (10):

$$V_i^{(L)'} = V_i^{(L)} + \eta_i \qquad (12)$$

wherein $V_i^{(L)}$ is the calculated value of the electromagnetic distribution point at the first measuring point, $\eta_i$ is the noise component added to the electromagnetic distribution, which noise component may be provided utilizing the random number. On the other hand, the superscript suffix L represents that the electromagnetic distribution is used in the training data.

As can be appreciated, since the electromagnetic field distribution as measured on the scalp may naturally contain noise component, it becomes possible to realize the live body internal condition expressing system resistive against the noise by making the neural network to preliminarily learn the data containing noise component.

Next, the fifth embodiment of the live body internal condition expressing system according to the present invention will be discussed with reference to FIG. 7. Like reference numerals to foregoing third and fourth embodiments of FIGS. 3 and 4 will represent like elements.

Figure 7:
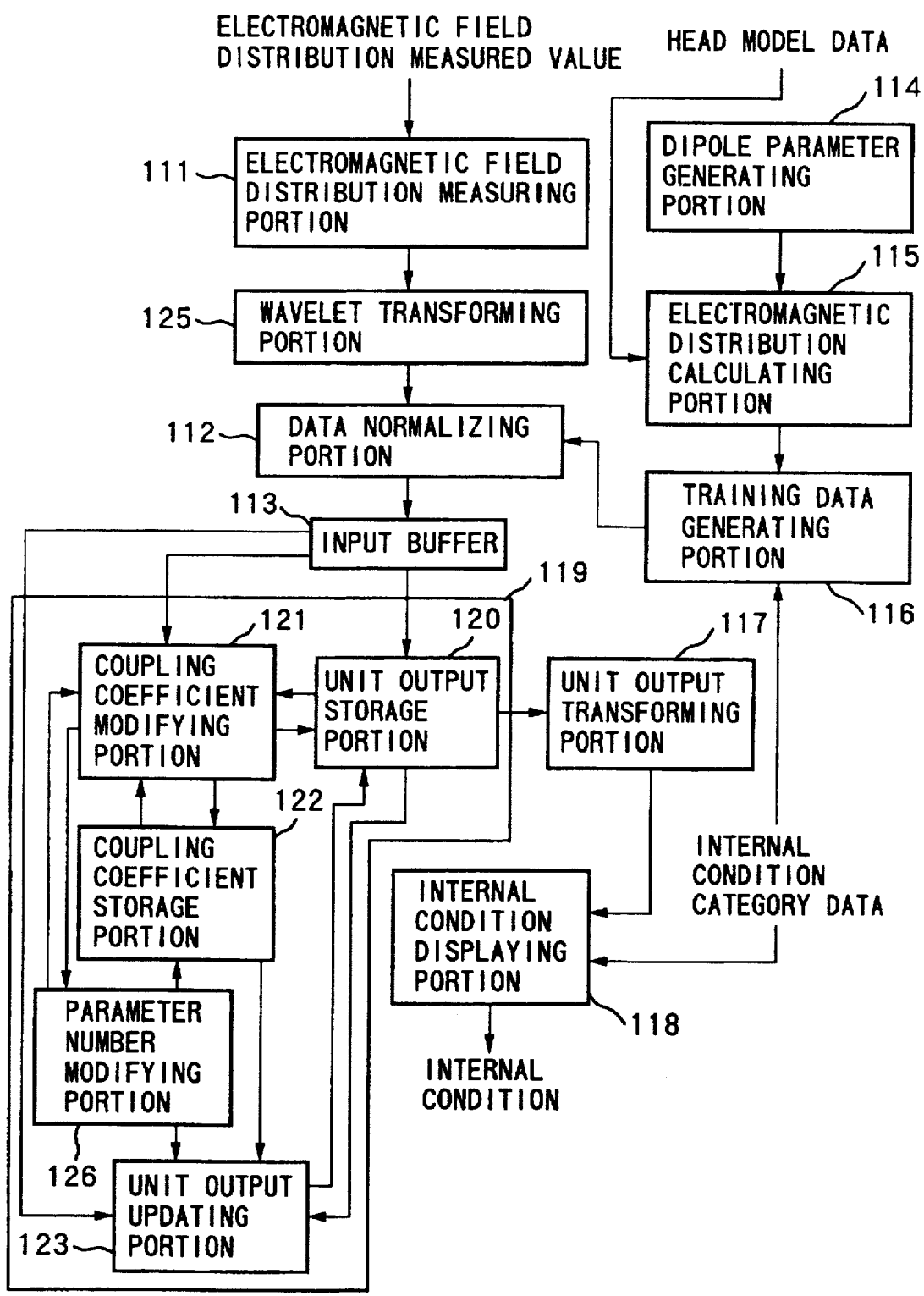
FIG. 7 is a block diagram of the fifth embodiment of the live body internal condition expressing system according to the present invention.

FIG. 7 is a block diagram showing the fifth embodiment of the live body internal condition expressing system according to the invention. In FIG. 7, the reference numeral 126 denotes a parameter number modifying portion for modifying number of the units forming the hidden layers of the neural network.

The parameter number modifying portion 126 modifies number of units in the hidden layer of the neural network, i.e. number of parameters, such as the coupling coefficients, so as to minimize the amount caused as description length of the neural network. When the number of data is according to the normalized distribution, the description length D+L can be expressed by the following equation.

$$DL = \frac{1}{2} N_t \log \frac{1}{N_t} \sum_{m=1}^{N_t} \sum_i [O_i^{(m)} - \tau_i^{(m)}]^2 + \frac{K}{2} \log N_t \qquad (13)$$

wherein $o_i^{(m)}$ and $\tau_i^{(m)}$ are respectively target outputs of the (m)th training data and thus are the output values of the neural network, $N_t$ is the number of training data, K is a number of parameters in the neural network. Once the number of parameters and the value of the coupling coefficient which makes the description length DL minimum, it becomes possible to restrict excessive adaption of the neural network to the noise component of the training data. Therefore, resistivity of the live body internal condition expressing system against the noise can be enhanced.

The description length as set forth above, has been discussed in detail in Rissanen, "Modeling by Shortest Data Description", Automatica. Vol. 14, pp 465 to 471, 1978.

It is also possible to employ Akaike's Information Criterion in place of the description length DL to make it possible to construct the live body internal condition expressing system having the equivalent function and effect. When the error of the data accords to the normal distribution, the Akaike's Information Criterion $I_{AIC}$ can be defined by:

$$I_{AIC} = N_t \log \frac{1}{N_t} \sum_{m=1}^{N_t} \sum_i [O_i^{(m)} - \tau_i^{(m)}]^2 + 2K \qquad (14)$$

Figure 9:
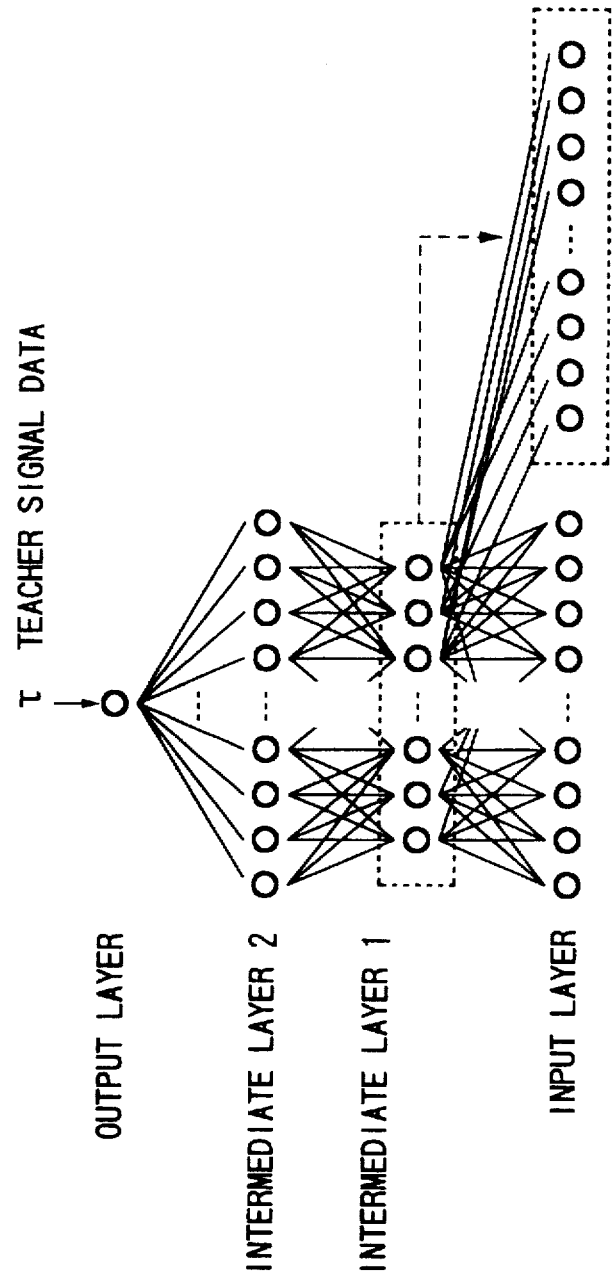
FIG. 9 is an explanatory illustration showing another example of construction of a neural network to be employed in the live body internal condition expressing system of the present invention.

FIG. 9 is an explanatory illustration showing one example of a construction of a re-current type neural network. While the foregoing discussion has been given for the neural network for learning the internal condition category, the neural network having no a structure having no feedback as shown in FIG. 9, when the re-current type is employed, the live body internal condition expressing system having the equivalent function and effect can be attained.

As set forth above, by employing the present invention, it becomes possible to instantly detect the content of the category which the testee wants to express, among two or three or more preliminarily prepared internal condition categories, on the basis of the scalp of the live body.

In the conventional method, it has taken several minutes to several hours in predicting the active region in the brain which is required for detecting the internal condition of the live body. In the present invention, this is significantly shortened to several msec. Also, while the conventional method employs the brain wave measured on the scalp of the live body as the training data of the neural network, the present invention employs the head model to significantly reduce the load on the testee. Furthermore, since the present invention employs the wavelet transformation in eliminating noise to enable setting of filter at different frequency band at different time regions to permit more flexible noise elimination. In addition, since the present invention performs learning of the neural network on the basis of the minimum description length principle or Akaike's Information Criterion standard, excessive adaption of the neural network to the training data can be prevented to permit construction of the neural network highly resistive against the noise.

The present invention is applicable in detection of will of the testee who cannot express the will due to handicap or any other reason. Also, it is possible to vary the situation setting in interactive matter with detecting the internal condition of the player in the television game or so forth to make game playing more exciting. Furthermore, the present invention may be use to detect the internal condition of surveillance in criminal investigation.

Although the invention has been illustrated and described with respect to exemplary embodiment thereof, it should be understood by those skilled in the art that the foregoing and various other changes, omissions and additions may be made therein and thereto, without departing from the spirit and scope of the present invention. Therefore, the present invention should not be understood as limited to the specific embodiment set out above but to include all possible embodiments which can be embodies within a scope encompassed and equivalents thereof with respect to the feature set out in the appended claims.

What is claimed is:

1. A system for expressing an internal condition of a live body which predicts the internal condition of the live body on the basis of an electromagnetic field distribution measured on a scalp of the live body, the system comprising:

electromagnetic field distribution measuring means for measuring electromagnetic field distribution caused on the scalp of the live body;

training data generating means for generating training data on the basis of an electromagnetic field distribution derived from head model data designating a head model, a predetermined dipole parameter, and internal condition category data describing a relationship between an active region of a brain of the live body and the internal condition of the live body, said brain being divided into a plurality of regions;

inferencing means for deriving a numeric value representative of the active region of the brain from the electromagnetic field distribution in the training data by employing a neural network comprising an input layer, an output layer and at least one hidden layer and having predetermined coupling coefficients representative of a coupling condition between each unit forming each layer; and transforming means for transforming the numeric value representative of the active region in the brain into an expression indicating of the internal condition of the live body;

said training data generating means generating 1 or −1 for each of said plurality of regions of said brain, based on the existence of the dipole in the region, as a correct numeric value representative of the correct active region of the brain described in said training data said inferencing means having a coupling coefficient modifying means for modifying said coupling coefficient of said neural network to reduce an error between (1) said correct numeric value representative of the correct active region of the brain described in said training data and (2) the numeric value derived by said neural network and indicative of the active region of the brain so that a numeric value indicative of the active region in the brain is derived by said neural network from the electromagnetic field distribution measured by said electromagnetic field distribution measuring means when said error becomes smaller than a predetermined reference value.

2. A live body internal condition expressing system as set forth in claim 1, which further comprises noise data adding means for generating a noise and adding the generated noise to said training data generated by said training data generating means.

3. A live body internal condition expressing system as set forth in claim 1, wherein said inferencing means employs a re-current type neural network.

4. A method for expressing a live body, in which an internal condition of the live body is predicted on the basis of an electromagnetic field distribution measured on a scalp of the live body, the method comprising the steps of:

dividing a brain into a plurality of regions in a head model;

generating training data on the basis of an electromagnetic field distribution derived from head model data designating the head model, a predetermined dipole parameter, and internal condition category data describing a relationship between the active region of the brain of the live body and the internal condition of the live body;

generating 1 or −1 for each of said plurality of said regions of the brain, by the existence of the dipole in the region, as a correct numeric value representative of the correct active region of the brain described in said training data, deriving a numeric value representative of the active region of the brain from the electromagnetic field distribution in the training data by employing a neural network comprising an input layer, an output layer and at least one hidden layer and having predetermined coupling coefficients representative of a coupling condition between each unit forming each layer;

modifying said coupling coefficient of said neural network to reduce an error between the correct numeric value representative of the correct active region of the brain described in said training data and the numeric value derived by said neural network and indicative of the active region of the brain; and deriving a numeric value indicative of the active region in the brain by said neural network taking the electromagnetic field distribution measured by said electromagnetic field distribution measuring means when said error becomes smaller than a predetermined reference value.

5. A system for predicting an internal condition of a live body for predicting the internal condition of the live body on the basis of an electromagnetic field distribution measured on a scalp of the live body, comprising:

electromagnetic field distribution measuring means for measuring an electromagnetic field distribution on the scalp of the live body;

wavelet transforming means for performing wavelet transformation for the electromagnetic field distribution measured by said electromagnetic field distribution measuring means for eliminating a noise component therefrom;

dipole parameter generating means for generating a dipole parameter employing a random number;

training data generating means for generating a plurality of training data on the basis of an electromagnetic field distribution derived from a head model data designating a head model and a predetermined dipole parameter and an internal condition category data describing a relationship between the active region of a brain and the internal condition of the live body said brain being divided into a plurality of regions;

inferencing means for deriving a numeric value representative of the active region of the brain from the electromagnetic field distribution in the training data with employing a neural network consisted of an input layer, an output layer and at least one hidden layer and having predetermined coupling coefficients representative of coupling condition between each unit forming each layer; and transforming means for transforming the numeric value representative of the active region in the brain output from said inferencing means into an expression indicative of the internal condition of the live body;

said training data generating means generating 1 or −1 for each of said plurality of regions of said brain, based on the existence of the dipole in the region, as a correct numeric value representative of the correct active region of the brain described in said training data.

6. A live body internal condition predicting system as set forth in claim 5, wherein said inferencing means has coupling coefficient modifying means for modifying said coupling coefficient of said neural network for reducing an error between the correct numeric value representative of the correct active region of the brain described in said training data and the numeric value derived by said neural network and indicative of the active region of the brain so that a numeric value indicative of the active region in the brain is derived by said neural network with taking the electromagnetic field distribution eliminated the noise when said error becomes smaller than a predetermined reference value.

7. A live body internal condition predicting system as set forth in claim 5, which further comprises noise data adding means for generating a noise and adding the generated noise to said training data generated by said training data generating means.

8. A live body internal condition predicting system as set forth in claim 5, which further comprises parameter number modifying portion for varying number of said coupling coefficients and number of said units forming said hidden layer to minimize a description length of said neural network, which description length is derived by dividing a product of a logarithm of number of the training data and number of parameters to be employed in said neural network by two, and multiplying the quotient with a value derived by subtracting one from a maximum logarithm likelihood.

9. A live body internal condition predicting system as set forth in claim 5, which further comprises parameter number modifying portion for varying number of said coupling coefficients and number of said units forming said hidden layer to minimize an Akaike's Information Criterion of said neural network, which Akaike's Information Criterion is derived by summing a value derived by multiplying the number of parameters to be employed in the neural network by 2 and a value derived by multiplying the maximum logarithm likelihood by −2.

10. A live body internal condition predicting system as set forth in claim 5, wherein said inferencing means employs a re-current type neural network.

11. A system for expressing an internal condition of a live body which predicts the internal condition of the live body on the basis of an electromagnetic field distribution measured on a scalp of the live body, the system comprising:

electromagnetic field distribution measuring means for measuring electromagnetic field distribution caused on the scalp of the live body;

training data generating means for generating training data on the basis of an electromagnetic field distribution derived from head model data designating a head model, a predetermined dipole parameter, and internal condition category data describing a relationship between an active region of a brain of the live body and the internal condition of the live body, said brain being divided into a plurality of regions;

inferencing means for deriving a numeric valve representative of the active region of the brain from the electromagnetic field distribution in the training data by employing a neural network comprising an input layer, an output layer and at least one hidden layer and having predetermined coupling coefficients representative of a coupling condition between each unit forming each layer, said inference means deriving a numeric value indicative of the active region in the brain by said neural network from the electromagnetic field distribution measured by said electromagnetic field distribution measuring means; and transforming means for transforming the numeric value representative of the active region in the brain output from said inferencing means into an expression indicative of the internal condition of the live body;

said training data generating means generating 1 or −1 for each of said plurality of regions of said brain, based on the existence of the dipole in the region, as a correct numeric value representative of the correct active region of the brain described in said training data.

12. A live body internal condition expressing system as set forth in claim 11, wherein said neural network in said inferencing means has said coupling coefficients at which an error between the correct numeric value representative of the correct active region of the brain described in said training data and the numeric value derived by said neural network and indicative of the active region of the brain becomes minimum.

13. A live body internal condition expressing system as set forth in claim 12, wherein said inferencing means has a coupling coefficient modifying means for modifying said coupling coefficient of said neural network for reducing an error between the correct numeric value representative of the correct active region of the brain described in said training data and the numeric value derived by said neural network and indicative of the active region of the brain to be minimum so that said inferencing means derives a numeric value indicative of the active region in the brain by said neural network with taking the electromagnetic field distribution measured by said electromagnetic field distribution measuring means when said error becomes smaller than a predetermined reference value.

14. A live body internal condition expressing system as set forth in claim 11, which further comprises normalizing means for normalizing said training data and the measured value of the electromagnetic field distribution measured by said electromagnetic field distribution measuring means.

15. A live body internal condition expressing system as set forth in claim 11, which further comprises noise eliminating means for eliminating noise component from the measured value of the electromagnetic field distribution measured by said electromagnetic field distribution measuring means.

16. A live body internal condition expressing system as set forth in claim 15, wherein said noise eliminating means comprises wavelet transforming means for performing wavelet transformation for removing noise from the measured value of the electromagnetic field distribution measured by said electromagnetic field distribution measuring means.

17. A live body internal condition expressing system as set forth in claim 11, which further comprises noise data adding means for generating a noise and adding the generated noise to said training data generated by said training data generating means.

18. A live body internal condition predicting system as set forth in claim 11, which further comprises parameter number modifying portion for varying number of said coupling coefficients and number of said units forming said hidden layer to minimize a description length of said neural network, which description length is derived by dividing a product of a logarithm of number of the training data and number of parameters to be employed in said neural network by two, and multiplying the quotient with a value derived by subtracting one from a maximum logarithm likelihood.

19. A live body internal condition predicting system as set forth in claim 11, which further comprises parameter number modifying portion for varying number of said coupling coefficients and number of said units forming said hidden layer to minimize an Akaike's Information Criterion of said neural network, which Akaike's Information Criterion is derived by summing a value derived by multiplying the number of parameters to be employed in the neural network by 2 and a value derived by multiplying the maximum logarithm likelihood by $-2$.

* * * * *